United States Patent
Brase et al.

(10) Patent No.: US 9,409,032 B2
(45) Date of Patent: Aug. 9, 2016

(54) SYSTEMS AND METHODS FOR MAKING AND USING CONNECTOR ASSEMBLY RETAINERS FOR ELECTRICAL STIMULATION SYSTEMS

(75) Inventors: Randall L. Brase, Castaic, CA (US); Roger Evan Furgang, Simi Valley, CA (US); Robert R. Tong, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 884 days.

(21) Appl. No.: 13/220,332

(22) Filed: Aug. 29, 2011

(65) Prior Publication Data

US 2012/0053646 A1  Mar. 1, 2012

Related U.S. Application Data

(60) Provisional application No. 61/378,613, filed on Aug. 31, 2010.

(51) Int. Cl.
*A61N 1/372* (2006.01)
*A61N 1/375* (2006.01)

(52) U.S. Cl.
CPC .................................. *A61N 1/3752* (2013.01)

(58) Field of Classification Search
CPC .................................................. A61N 1/3752
USPC ...................................................... 607/36–38
See application file for complete search history.

(56) References Cited

U.S. PATENT DOCUMENTS

| | | | |
|---|---|---|---|
| 6,181,969 B1 | 1/2001 | Gord | |
| 6,321,126 B1 | 11/2001 | Kuzma | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,662,035 B2 * | 12/2003 | Sochor | 600/378 |
| 6,741,892 B1 | 5/2004 | Meadows et al. | |
| 7,244,150 B1 | 7/2007 | Brase | |
| 7,437,193 B2 | 10/2008 | Parramon | |
| 7,672,734 B2 | 3/2010 | Anderson | |
| 7,736,191 B1 * | 6/2010 | Sochor | 607/116 |
| 7,761,165 B1 | 7/2010 | He | |
| 7,949,395 B2 | 5/2011 | Kuzma | |
| 7,974,706 B2 | 7/2011 | Moffitt | |
| 8,206,180 B1 * | 6/2012 | Kast et al. | 439/668 |
| 2005/0165465 A1 | 7/2005 | Pianca | |
| 2006/0030918 A1 | 2/2006 | Chinn | |

(Continued)

OTHER PUBLICATIONS

International Search Report and Written Opinion, International Application No. PCT/US2011/049594, mailed Nov. 30, 2011.

*Primary Examiner* — George Evanisko
(74) *Attorney, Agent, or Firm* — Lowe Graham Jones PLLC; Bruce E. Black

(57) ABSTRACT

A control module for providing electrical stimulation of patient tissue includes a header disposed over an electrical interface. A connector assembly retainer is disposed in the header and coupled to the electrical interface. The connector assembly retainer includes a plurality of channels and a plurality of apertures defined at one end of the connector assembly retainer. Each of a plurality of connector assemblies is disposed in a different one of the plurality of channels of the connector assembly retainer. Each of the plurality of connector assemblies is configured and arranged for receiving a portion of a lead or lead extension and coupling the lead or lead extension to the electronic subassembly.

20 Claims, 11 Drawing Sheets

(56) References Cited

U.S. PATENT DOCUMENTS

2007/0150036 A1 6/2007 Anderson
2007/0219595 A1 9/2007 He
2008/0071320 A1 3/2008 Brase
2010/0070012 A1 3/2010 Chinn

* cited by examiner

SYSTEMS AND METHODS FOR MAKING AND USING CONNECTOR ASSEMBLY RETAINERS FOR ELECTRICAL STIMULATION SYSTEMS

CROSS-REFERENCE TO RELATED APPLICATIONS

This application claims the benefit under 35 U.S.C. §119 (e) of U.S. Provisional Patent Application Ser. No. 61/378,613 filed on Aug. 31, 2010, which is incorporated herein by reference.

FIELD

The present invention is directed to the area of implantable electrical stimulation systems and methods of making and using the systems. The present invention is also directed to implantable control modules that include one or more connector assemblies disposed in a connector assembly retainer, as well as methods of making and using the control modules, connector assemblies, connector assembly retainers, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a control module for providing electrical stimulation of patient tissue includes a control module housing having an outer surface. An electronic subassembly is disposed in the control module housing. An electrical interface is disposed along the outer surface of the control module housing and is coupled to the electronic subassembly. A header is disposed along the outer surface of the control module housing over the electrical interface. The header defines a plurality of ports. A connector assembly retainer is disposed in the header and coupled to the electrical interface. The connector assembly retainer has a first end, a second end, and a longitudinal axis. The connector assembly retainer includes a plurality of channels each extending along the longitudinal axis of the connector assembly retainer. The connector assembly retainer further includes a plurality of apertures defined at the second end of the connector assembly retainer such that each of the plurality of apertures is aligned axially with a different one of the plurality of channels. Each of the plurality of ports defined in the header is aligned with a different one of the plurality of apertures defined at the second end of the connector assembly retainer. A plurality of connector assemblies are each configured and arranged for receiving a lead or lead extension. Each of the plurality of connector assemblies is disposed in a different one of the plurality of channels of the connector assembly retainer. Each of the plurality of connector assemblies includes a connector housing defining a port at one end of the connector assembly. The port is configured and arranged for receiving a portion of the lead or lead extension. A plurality of spaced-apart connector contacts are disposed in the port defined by the connector housing. The plurality of connector contacts are each coupled to the electronic subassembly. The plurality of connector contacts are configured and arranged to couple to terminals disposed on the lead or lead extension. At least one non-conductive spacer is disposed between adjacent connector contacts of the plurality of connector contacts.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable control modules that include one or more connector assemblies disposed in a connector assembly retainer, as well as methods of making and using the control modules, connector assemblies, connector assembly retainers, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,672,734; 7,761,165; and 7,974,706, and U.S. Patent Applications Publication Nos. 2003/0114905, 2005/0165465, 2007/0150036; 2007/0219595; and 2008/0071320, all of which are incorporated by reference.

Figure 1:
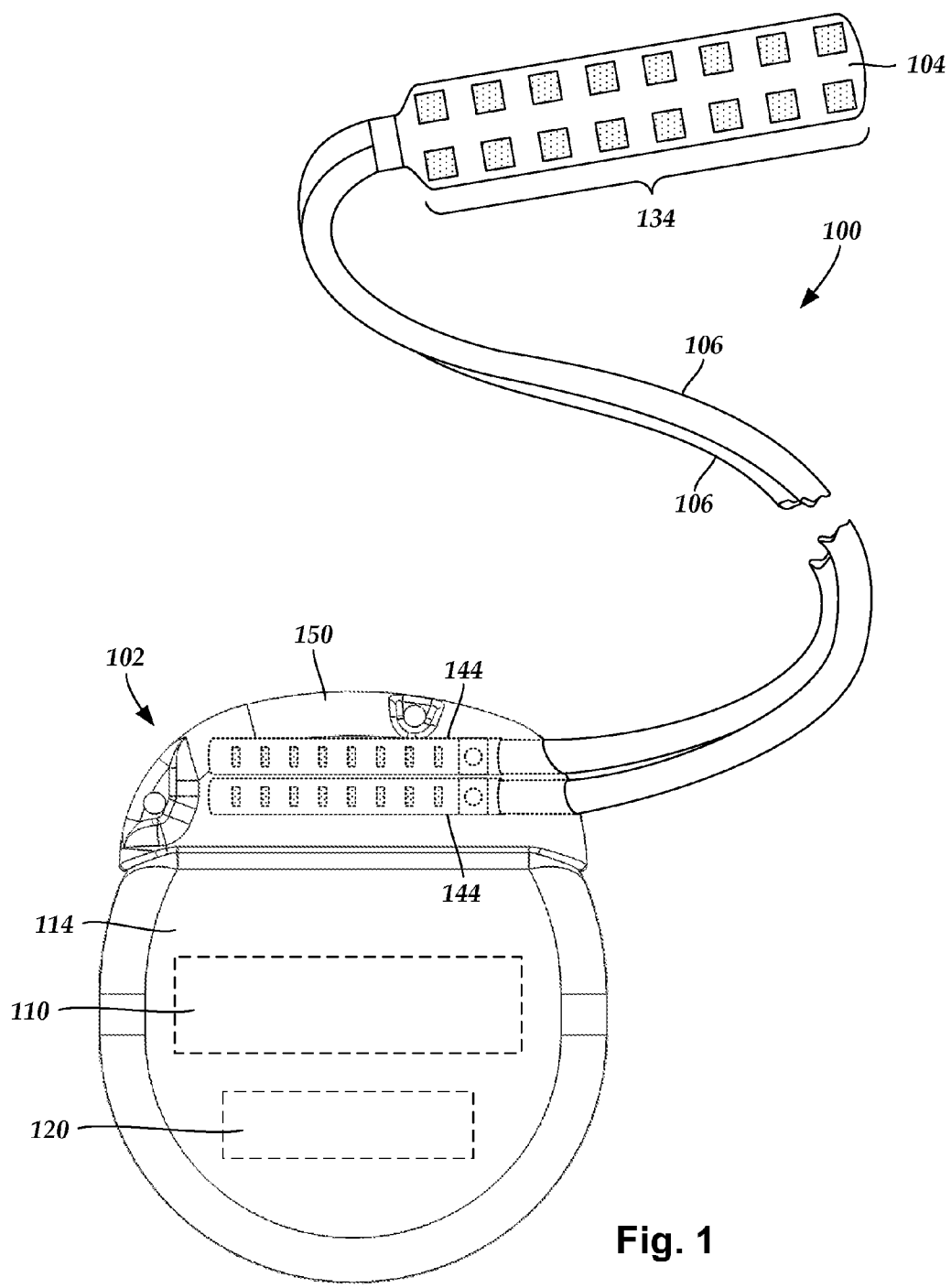
FIG. 1 is a schematic view of one embodiment of an electrical stimulation system that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102, a paddle body 104, and one or more lead bodies 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 316 in FIG. 3A) disposed in the connector assembly 144 and terminals (e.g., 310 in FIG. 3A) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
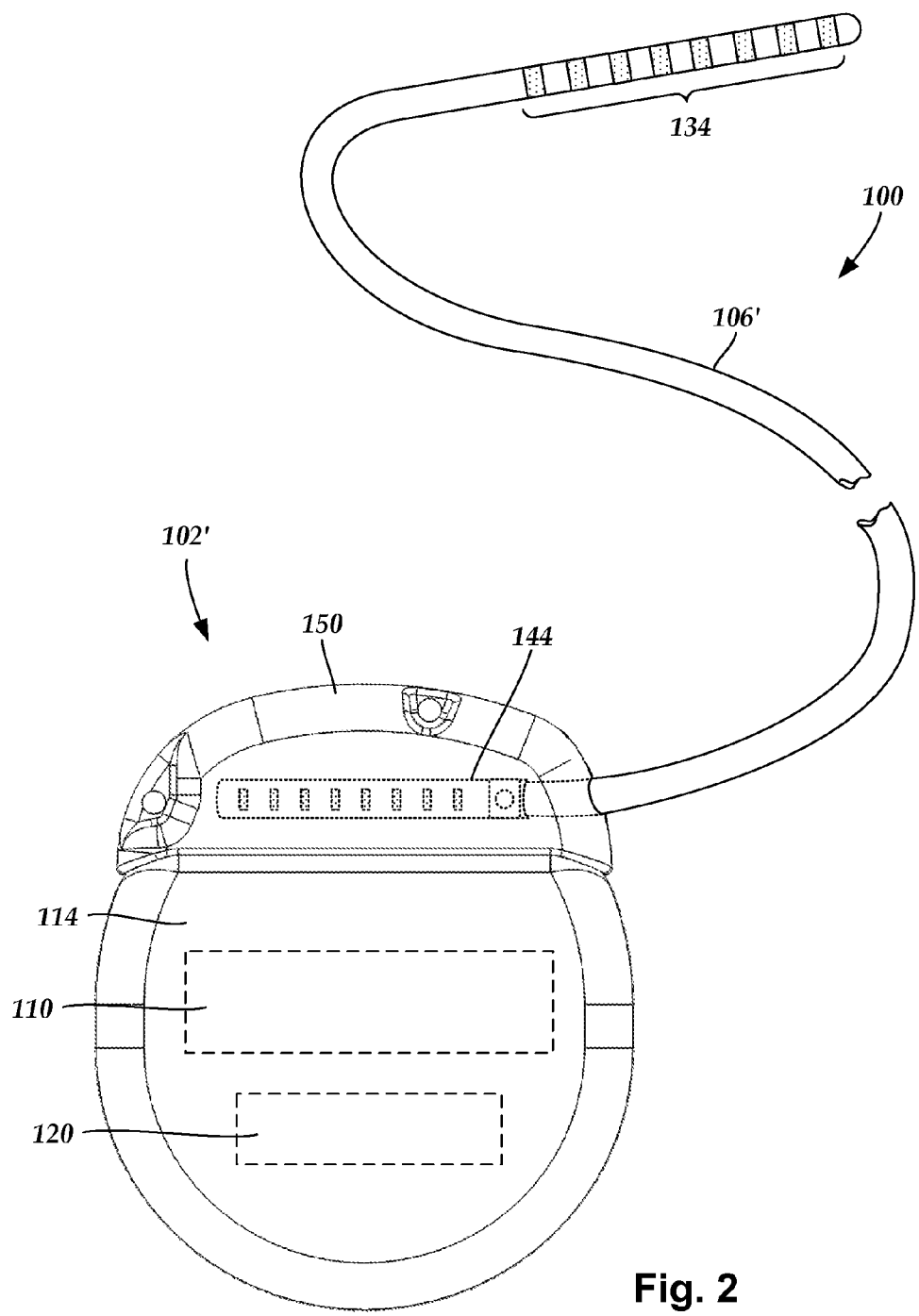
FIG. 2 is a schematic view of another embodiment of an electrical stimulation system that includes a percutaneous lead body coupled to a control module via a lead body, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of a lead body 106' forming a percutaneous lead, as illustrated in FIG. 2. The percutaneous lead may be isodiametric along the length of the lead body 106''. The lead body 106' can be coupled with a control module 102' with a single connector assembly 144.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 134 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A) are typically disposed at the proximal end of the one or more lead bodies 106 for connection to corresponding conductive contacts (e.g., 316 in FIG. 3A) in connector assemblies (e.g., 144 in FIG. 1) disposed on, for example, the control module 102 (or to other devices, such as conductive contacts on a lead extension, an operating room cable, a splitter, an adaptor, or the like).

Conductive wires (not shown) extend from the terminals (e.g., 310 in FIG. 3A) to the electrodes 134. Typically, one or more electrodes 134 are electrically coupled to a terminal (e.g., 310 in FIG. 3A). In some embodiments, each terminal (e.g., 310 in FIG. 3A) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

Figure 3A:
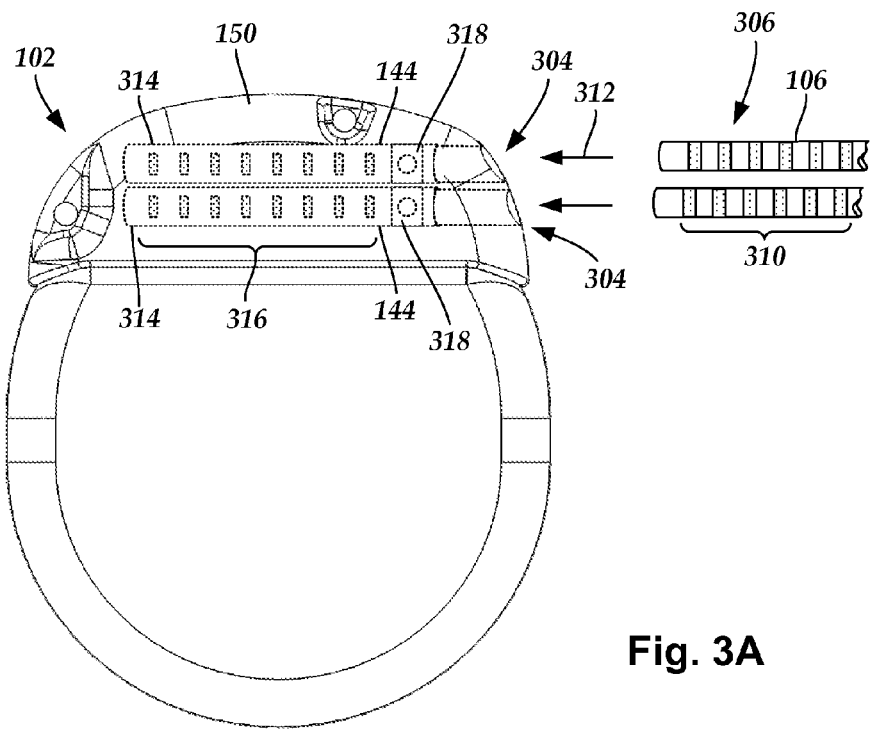
FIG. 3A is a schematic view of one embodiment of a plurality of connector assemblies disposed in the control module of FIG. 1, the connector assemblies configured and arranged to receive the proximal portions of the lead bodies of FIG. 1, according to the invention.
Figure 3B:
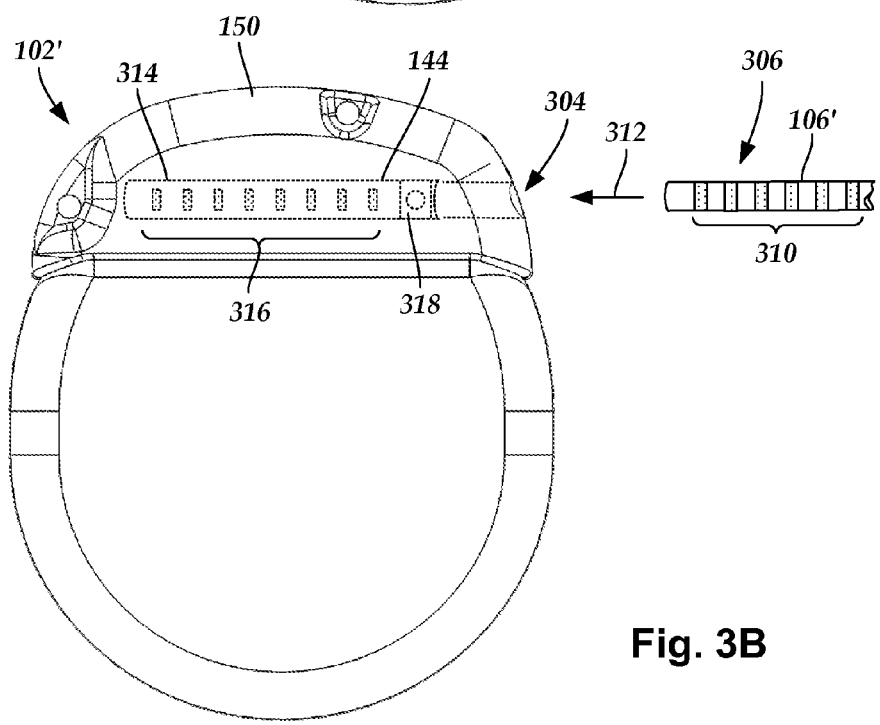
FIG. 3B is a schematic view of one embodiment of a connector assembly disposed in the control module of FIG. 2, the connector assembly configured and arranged to receive the proximal portion of one of the lead body of FIG. 2, according to the invention.

FIG. 3A is a schematic side view of one embodiment of a plurality of connector assemblies 144 disposed on the control module 102. In at least some embodiments, the control module 102 includes two connector assemblies 144. In at least some embodiments, the control module 102 includes four connector assemblies 144. In FIG. 3A, proximal ends 306 of the plurality of lead bodies 106 are shown configured and arranged for insertion to the control module 102. FIG. 3B is a schematic side view of one embodiment of a single connector assembly 144 disposed on the control module 102'. In FIG. 3B, the proximal end 306 of the single lead body 106' is shown configured and arranged for insertion to the control module 102'.

In FIGS. 3A and 3B, the one or more connector assemblies 144 are disposed in the header 150. In at least some embodiments, the header 150 defines one or more ports 304 into which the proximal end(s) 306 of the one or more lead bodies 106/106' with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured and arranged to fasten the corresponding lead body 106/106' to the connector assembly 144 when the lead body 106/106' is inserted into the connector assembly 144 to prevent undesired detachment of the lead body 106/106' from the connector assembly 144. For example, the retaining element 318 may include an aperture through which a fastener (e.g., a set screw, pin, or the like) may be inserted and secured against an inserted lead body 106/106'.

When the one or more lead bodies 106/106' are inserted into the one or more ports 304, the connector contacts 316 can be aligned with the terminals 310 disposed on the one or more lead bodies 106/106' to electrically couple the control module 102 to the electrodes (134 of FIG. 1) disposed at a distal end of the one or more lead bodies 106. Examples of connector assemblies in control modules are found in, for example, U.S. Pat. No. 7,244,150 and U.S. patent application Ser. No. 11/532,844, which are incorporated by reference.

Figure 3C:
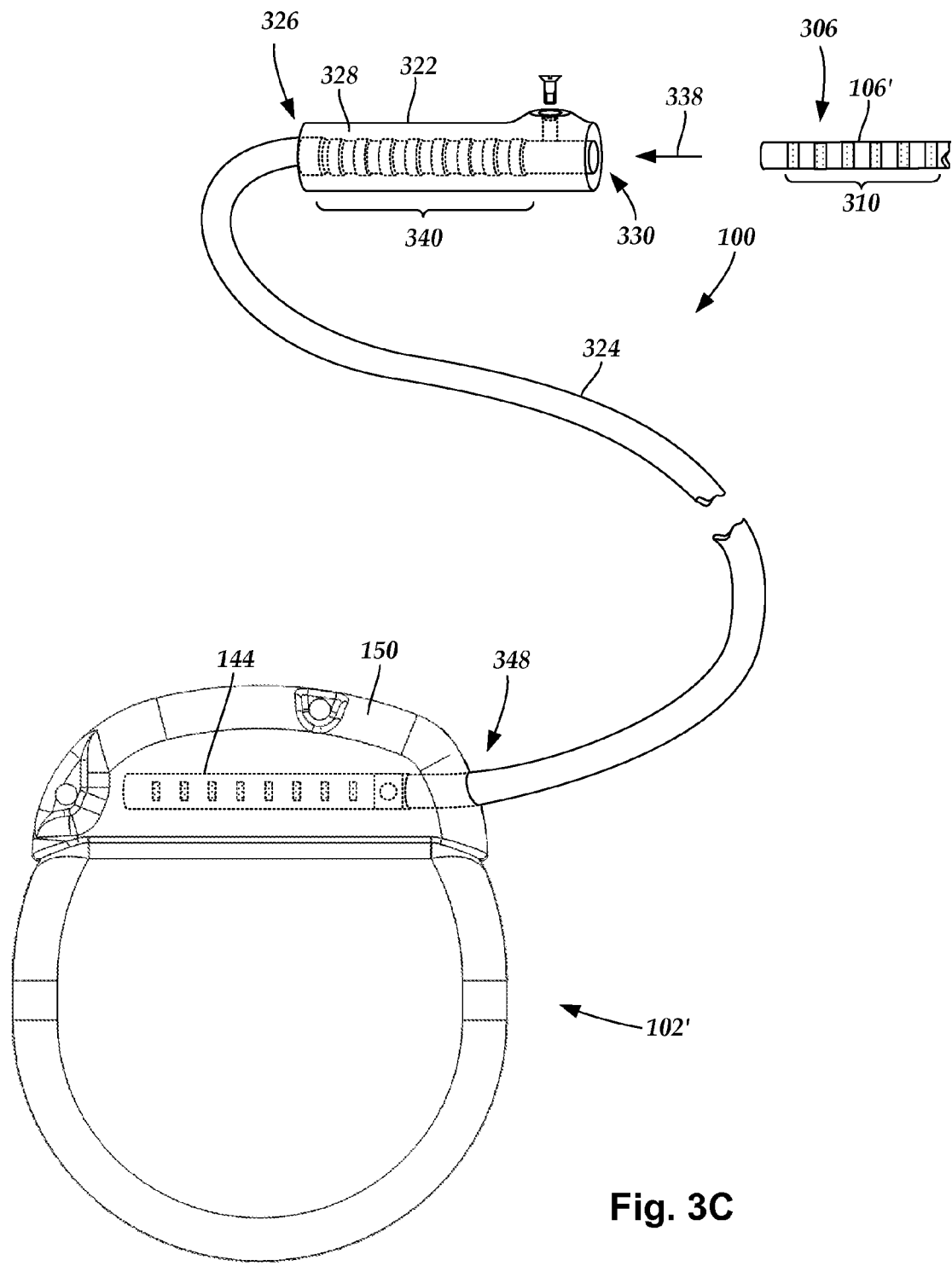
FIG. 3C is a schematic view of one embodiment of a proximal portion of the lead body of FIG. 2, a lead extension, and the control module of FIG. 2, the lead extension configured and arranged to couple the lead body to the control module, according to the invention.

In at least some embodiments, the electrical stimulation system includes one or more lead extensions. The one or more lead bodies 106/106' can be coupled to one or more lead extensions which, in turn, are coupled to the control module 102/102'. In FIG. 3C, a lead extension connector assembly 322 is disposed on a lead extension 324. The lead extension connector assembly 322 is shown disposed at a distal end 326 of the lead extension 324. The lead extension connector assembly 322 includes a contact housing 328. The contact housing 328 defines at least one port 330 into which a proximal end 306 of the lead body 106' with terminals 310 can be inserted, as shown by directional arrow 338. The lead extension connector assembly 322 also includes a plurality of connector contacts 340. When the lead body 106' is inserted into the port 330, the connector contacts 340 disposed in the contact housing 328 can be aligned with the terminals 310 on the lead body 106 to electrically couple the lead extension 324 to the electrodes (134 of FIG. 1) disposed at a distal end (not shown) of the lead body 106'.

The proximal end of a lead extension can be similarly configured and arranged as a proximal end of a lead body. The lead extension 324 may include a plurality of conductive wires (not shown) that electrically couple the connector contacts 340 to terminal on a proximal end 348 of the lead extension 324. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector assembly disposed in another lead extension. In other embodiments (as shown in FIG. 3C), the proximal end 348 of the lead extension 324 is configured and arranged for insertion into the connector assembly 144 disposed on the control module 102'.

It will be understood that the control modules 102/102' can receive either lead bodies 106/106' or lead extensions 324. It will also be understood that the electrical stimulation system 100 can include a plurality of lead extensions 224. For example, each of the lead bodies 106 shown in FIGS. 1 and 3A can, alternatively, be coupled to a different lead extension 224 which, in turn, are each coupled to different ports of a two-port control module, such as the control module 102 of FIGS. 1 and 3A.

As discussed above with reference to FIGS. 1 and 2, the control module 102/102' typically includes a connector assembly 144 into which the proximal end of the one or more lead bodies 106/106' (or the proximal end of one or more lead extensions 324) can be plugged to make an electrical connection via connector contacts disposed in the connector assembly 144. The connector contacts are typically electrically coupled to the electronic subassembly 110.

As also discussed above with reference to FIG. 1, in at least some embodiments the one or more connector assemblies 144 are disposed in the header 150. In at least some embodiments, the header 150 at least partially covers an electrical interface (see e.g., electrical interface 602 of FIG. 6A) disposed on an outer surface of the housing (114 of FIG. 1) of the control module 102. In at least some embodiments, the electrical interface 602 is electrically coupled to the electronic subassembly 110.

The connector contacts 316 are typically electrically coupled to the electronic subassembly 110 via the electrical interface 602 and one or more control module conductors (e.g., one or more feedthrough members, one or more feedthrough pins, and the like or combinations thereof).

Figure 10:
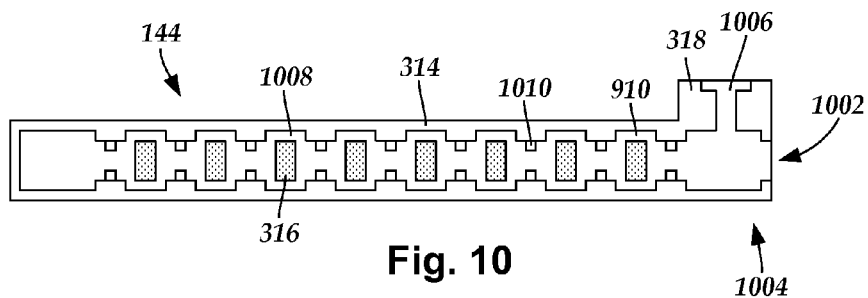
FIG. 10 is a schematic longitudinal cross-sectional view of one embodiment of a connector assembly suitable for use with the electrical stimulation system of FIGS. 1 and 2, according to the invention.

FIG. 10 is a schematic longitudinal cross-sectional view of one embodiment of the connector assembly 144. The connector assembly 144 includes the connector housing 314 into which a lead or lead extension can be inserted via a port 1002 at a distal end 1004 of the connector housing 314. A retaining element 318 is coupled to the connector housing 314. The retaining element 318 defines an aperture 1006 through which a fastener (e.g., a set screw, pin, or the like) may be inserted and secured against a lead body or lead extension when the lead or lead extension is inserted into the port 1002. The connector housing 314 defines a plurality of axially-spaced-apart pockets, such as pocket 1008, that receive connector contacts, such as the connector contact 316. The pockets 1008 are separated from one another by one or more non-conductive spacers (or seals), such as spacer 1010, to prevent electrical contact between adjacent connector contacts 316. As discussed above, when a proximal end of a lead or lead extension is inserted into the port 1002, terminals disposed on the inserted lead or lead extension align with the connector contacts 316, thereby establishing an electrical connection between the electronic subassembly 110 of the control module 102 and the electrodes 134 of the lead.

Figure 4:
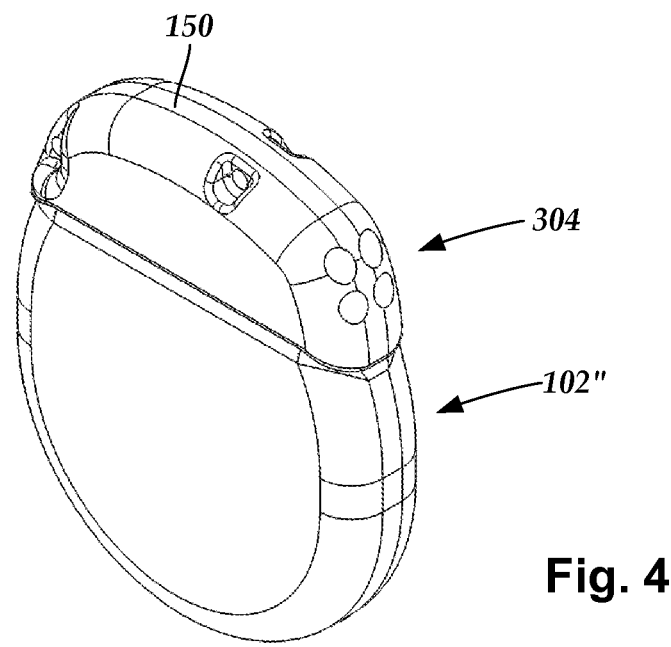
FIG. 4 is a schematic perspective view of ports defined in a header of the control module of FIG. 1, according to the invention.

FIG. 4 is a schematic perspective view of a control module 102". The header 150 of the control module 102" defines four header ports 404. Collectively, the header ports 404 are configured and arranged to each receive one or more lead bodies 106 or one or more lead extensions (e.g., lead extension 324 of FIG. 3B), or both. The header 150 can define any suitable number of header ports 404 including, for example, one, two, three, four, five, six, seven, eight, or more header ports 404. In FIG. 4, the header 150 is shown defining four header ports 404. Thus, in at least some embodiments, the control module 102" of FIG. 4 is configured and arranged to receive up to four lead bodies 106 or lead extensions 224, or a combination of both.

The header ports 404 can be defined in the header 150 in any suitable arrangement. In preferred embodiments, each of the header ports 404 are configured and arranged to align with one of the ports 302 of the one or more connector assemblies 144 disposed in the header 150. For example, in at least some embodiments, four connector assemblies 144 are disposed in the header 150 such that four header ports 404 defined in the header 150 align with the four ports 302 of the four connector assemblies 144. In at least some embodiments, the number of header ports 404 is no greater than the number of connector assemblies 144. In at least some embodiments, the number of header ports 404 is no less than the number of connector assemblies 144. In at least some embodiments, the number of header ports 404 is equal to the number of connector assemblies 144.

At least some headers 150 are formed using a casting process. During a typical header casting process, the one or more connector assemblies 144 may be disposed in the header 150 such that the one or more connector assemblies 144 are unrestrained (e.g., the one or more connector assemblies 144 float freely within the header 150 as the header 150 is curing). Consequently, the one or more of the connector assemblies 144 may set at an undesired angle or an undesired position that reduces, or eliminates, the ability of terminals of an inserted lead body or lead extension to make contact with corresponding connector contacts.

It may be advantageous to be able to maintain a relative positioning of the one or more connector assemblies 144 during formation of the header 150 to provide consistent spacing and orientation of the one or more connector assemblies 144 to facilitate proper registration of a lead body or a lead extension in the one or more connector assemblies 144. As described herein, the one or more connector assemblies 144 can be disposed in a connector assembly retainer. In at least some embodiments, the one or more connector assemblies are disposed in the connector assembly retainer such that the one or more connector assemblies maintain a constant positioning with respect to the header 150 during the header casting process.

In at least some embodiments, the connector assembly retainer defines one or more channels each configured and arranged to receive the one or more connector assemblies 144. In at least some embodiments, the one or more channels are each configured and arranged to receive one of the one or more connector assemblies 144. In preferred embodiments, the one or more connector assemblies 144 are each inserted into a different one of the channels such that the ports of the connector assemblies 144 open to a distal end of the connector assembly retainer.

In at least some embodiments, the received connector assemblies 144 are permanently disposed in the channels. For example, in at least some embodiments, the received connector assemblies 144 are affixed to the channels using an adhesive. In preferred embodiments, the received connector assemblies 144 are releasably disposed in the channels.

The connector assembly retainer can define any suitable number of channels including, for example, one, two, three, four, five, six, seven, eight, or more channels. In at least some embodiments, the number of channels is equal to the number of connector assemblies 144. In at least some embodiments, the number of channels is no fewer than the number of connector assemblies 144. In at least some embodiments, the number of channels is no greater than the number of connector assemblies 144.

Figure 5A:
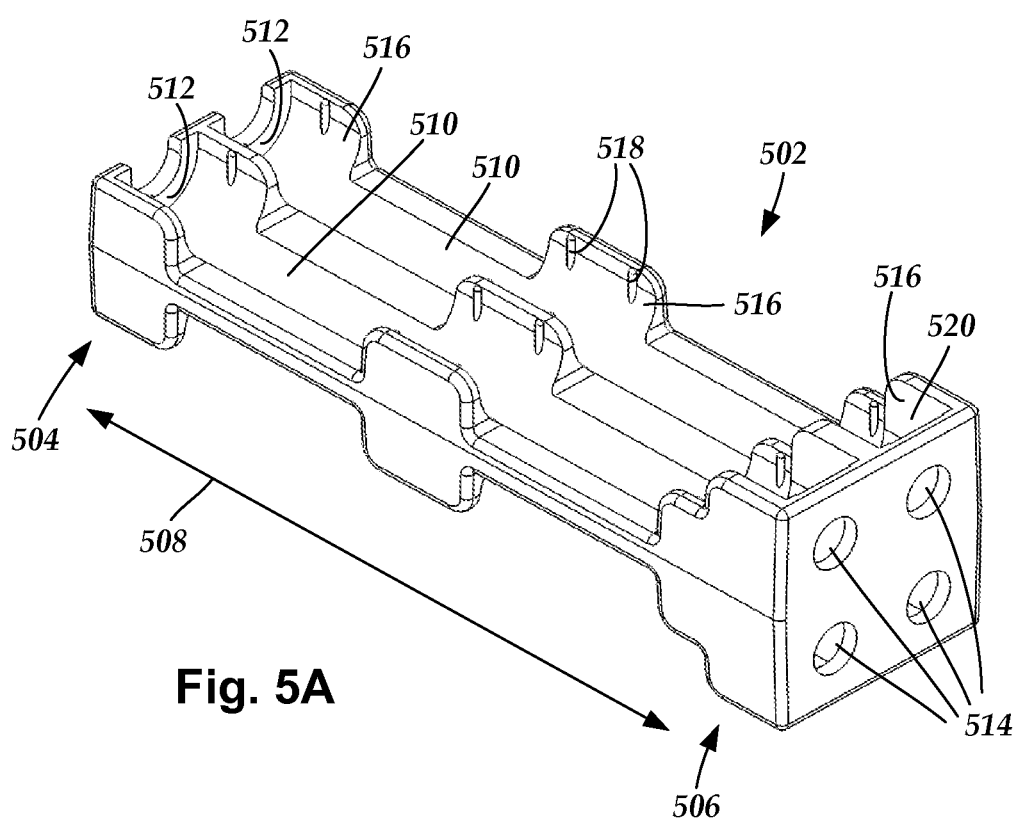
FIG. 5A is a schematic perspective view of one embodiment of a connector assembly retainer suitable for use with the control module of FIG. 1, according to the invention.
Figure 5B:
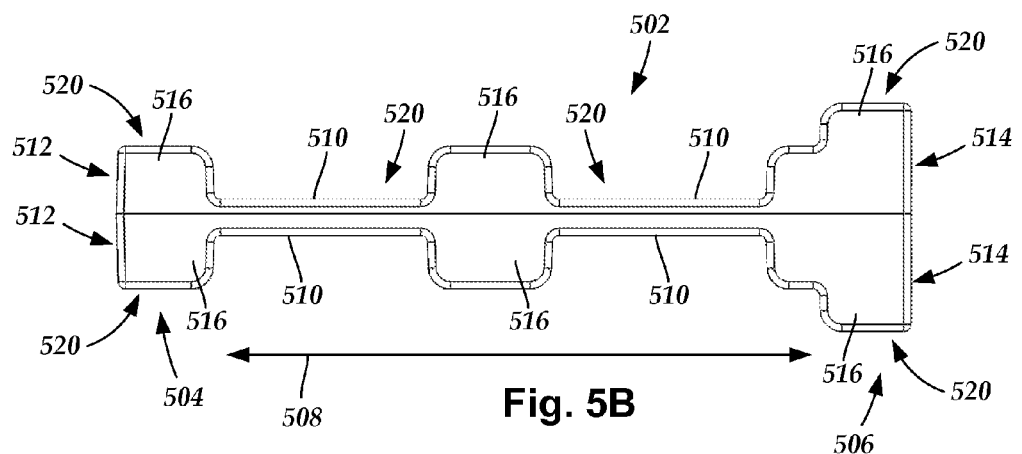
FIG. 5B is a schematic side view of one embodiment of the connector assembly retainer of FIG. 5A, according to the invention.
Figure 5C:
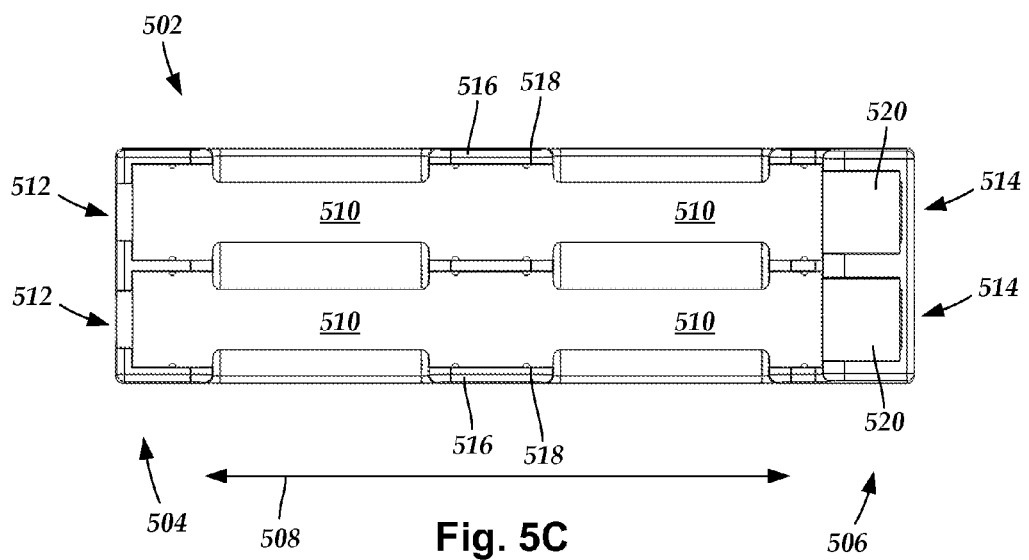
FIG. 5C is a schematic top view of one embodiment of the connector assembly retainer of FIG. 5A, according to the invention.

In at least some embodiments, the connector assembly retainer is configured and arranged to receive up to four connector assemblies 144. FIG. 5A is a schematic perspective view of one embodiment of a connector assembly retainer 502 suitable for use with the control module 102. FIG. 5B is a schematic side view of one embodiment of the connector assembly retainer 502. FIG. 5C is a schematic top view of one embodiment of the connector assembly retainer 502. The connector assembly retainer 502 has a proximal end 504, a distal end 506, and a longitudinal axis 508. The connector assembly retainer 502 includes channels 510. In at least some embodiments, at least one of the channels 510 extends along the longitudinal axis 508 of the connector assembly retainer 502.

In at least some embodiments, the connector assembly retainer 502 includes an end stop 512 disposed at the proximal end 504 of at least one of the channels 510. In at least some embodiments, the one or more end stops 512 prevent axial sliding of the one or more connector assemblies 144 toward the proximal end 504 of the connector assembly retainer 502 when the one or more connector assemblies 144 are inserted into the channels 510. In at least some embodiments, the connector assembly retainer 502 includes a partition 520 that separates at least one of the channels 510 from the remaining channels 510. In FIGS. 5A-5D the connector assembly retainer 502 includes four channels 510 and the partition 520 physically separates two of the channels 510 from the remaining two channels 510.

In at least some embodiments, the connector assembly retainer 502 defines one or more apertures 514 at the distal end 506 of at least one of the channels 510. In at least some embodiments, the one or more apertures 514 prevent axial sliding of the one or more connector assemblies 144 toward the distal end 506 of the connector assembly retainer 502 when the one or more connector assemblies 144 are inserted into the channels 510.

In at least some embodiments, at least one of the one or more apertures 514 is axially-aligned with at least one of the channels 510 such that when the lead body or lead extension is extended through one of the at least one of the apertures 514, the lead body or lead extension is received by the axially-aligned channel 510. In at least some embodiments, the one or more apertures 514 are arranged in a configuration such that, when the connector assembly retainer 502 is disposed on the control module 102, the one or more apertures 514 are aligned with the one or more ports 304 defined in the header 150.

As discussed above the one or more connector assemblies 144 can be releasably disposed in the connector assembly retainer 502. The one or more connector assemblies 144 can be releasably disposed in the connector assembly retainer 502 in any suitable manner including, for example, an interference fit, a snap connection, one or more binders, or the like or combinations thereof.

In at least some embodiments, the connector assembly retainer 502 includes one or more retention features that facilitate the releasable retention of one or more of the connector assemblies 144 within the connector assembly retainer 502. In at least some embodiments, the one or more retention features include one or more enhanced wall regions, such as enhanced wall regions 516. In at least some embodiments, the one or more enhanced wall regions 516 provide a snap connection with received connectors 144 by temporarily expanding during insertion of the connector assemblies 144 into the channels 510 or removal of the connector assemblies 144 therefrom. In at least some embodiments, the enhanced wall regions 516 include one or more extended portions of walls of the channels 510 that extend a transverse circumference of one or more portions of the channel 510. In at least some embodiments, the extended wall features 516 include one or more features that are coupled to the channels 510 and that effectively extend a transverse circumference of one or more portions of the channels 510.

In at least some embodiments, the one or more retention features include one or more projections (e.g., one or more knobs, ridges, features, domes, bulges, juts, outthrusts, spurs, shelves, protuberances, or the like or combinations thereof), such as projections 518, disposed along at least one of the channels 510. In at least some embodiments, at least one of the one or more projections 518 is configured and arranged to mate with correspondingly sized and arranged indentations (e.g., grooves, dimples, cracks, fissures, notches, dents, depressions, gouges, incisions, nicks, clefts, gaps, mills, ruts, scores, cuts, trenches, scratches, channels, or the like or combinations thereof) (not shown) disposed on an outer surface of the connector housing 314.

In at least some embodiments, a single projection 518 is disposed along a given transverse cross-section of at least one of the channels 510. In at least some embodiments, at least two projections 518 are disposed along a given transverse cross-section of at least one of the channels 510. In at least some embodiments, at least one of the projections 518 is disposed on at least one of the enhanced wall regions 516.

In at least some embodiments, at least one of the channels 510 defines a pocket 520 configured and arranged to receive the retaining element 318 of the connector assembly 144. In at least some embodiments, the pocket 520 is disposed at the distal end 506 of the connector assembly retainer 502. In at least some embodiments, the pocket 506 is disposed proximal to the one or more apertures 514.

Figure 5D:
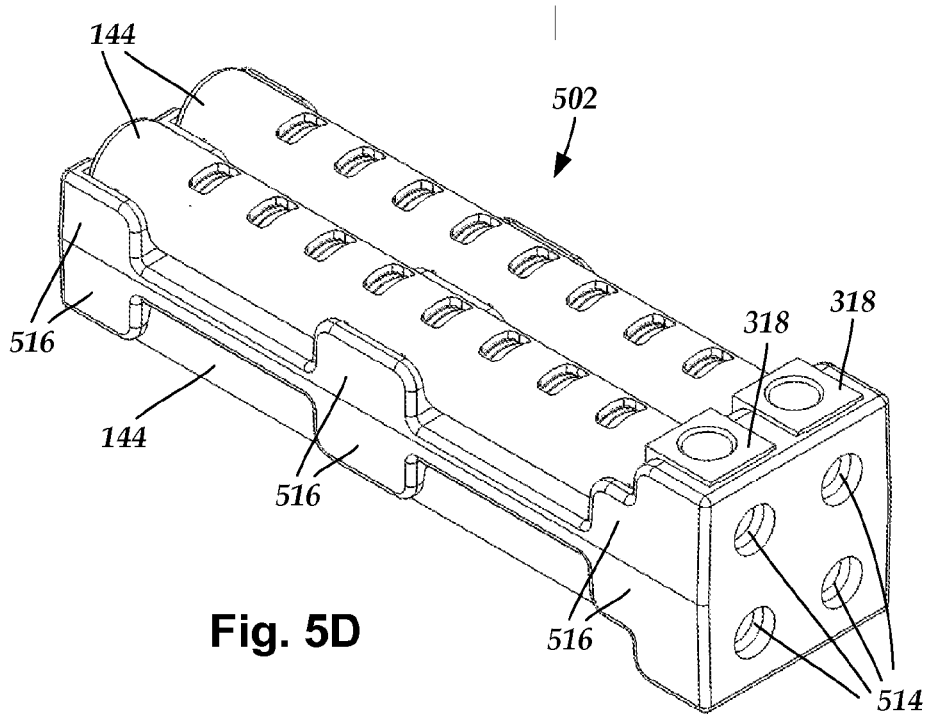
FIG. 5D is a schematic perspective view of one embodiment of connector assemblies disposed in the connector assembly retainer of FIG. 5A, according to the invention.

In at least some embodiments, at least some of the channels 510 is configured and arranged to receive one connector assembly 144. FIG. 5D is a schematic perspective view of one embodiment of connector assemblies 144 disposed in the connector assembly retainer 502. As shown in FIG. 5D, the connector assemblies 144 can be positioned parallel to one another. As also shown in FIG. 5D, the connector assemblies 144 can be axially aligned with one another. In at least some embodiments, at least one of the channels 510 has a length that is equal to a length of at least one of the connector assemblies 144. In at least some embodiments, at least one of the connector assemblies 144 can be positioned within one of the channels 510 such that the retaining element 318 is exposed to provide access to the retaining element 318 (e.g., for insertion or removal of a fastener used to retain a proximal end of a lead body or lead extension within the connector assembly 144).

In FIGS. 5D-6C the connector assembly retainer 502 is shown housing connector assemblies 144 in a two-by-two configuration. It will be understood that the connector assemblies 144 can be housed in any suitable configuration, such as a one-by-four configuration (not shown), or a one-by-two-by-one orientation (or any alternate combination thereof) (not shown). In FIGS. 5D-6C the connector assembly retainer 502 is shown housing connector assemblies 144 such that two of the channels 510 are open along a first side of the connector assembly retainer 502 and the other two channels 510 are open along a second side of the connector assembly retainer 502 that is opposite from first side. It will be understood that the connector assembly retainer 502 can be arranged such that all, or a portion, of the channels 510 are open along any side of the connector assembly connector 502.

In at least some embodiments, each of the channels 510 receives one of the connector assemblies 144. In at least some embodiments, one or more of the channels 510 receives one or more of the connector assemblies 144 while one or more of the channels 510 remains empty. In at least some embodiments, at least one of the one or more empty channels 510 does not include an axially-aligned aperture 314. In at least some embodiments, at least one of the one or more empty channels 510 includes a covered axially-aligned aperture 314.

Figure 6A:
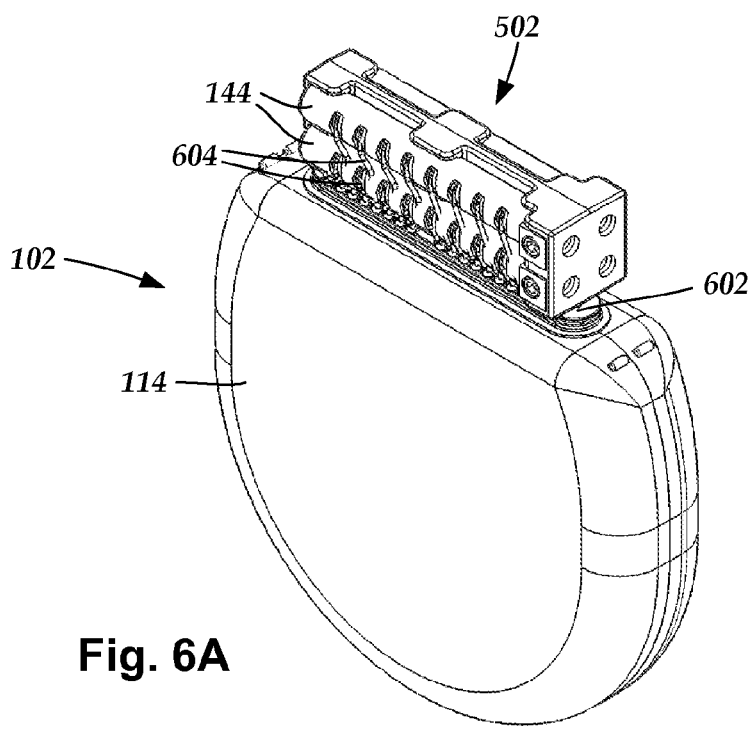
FIG. 6A is a schematic perspective view of one embodiment of connector assemblies disposed in the connector assembly retainer of FIG. 5A which, in turn, is disposed on the control module of FIG. 1, according to the invention.
Figure 6B:
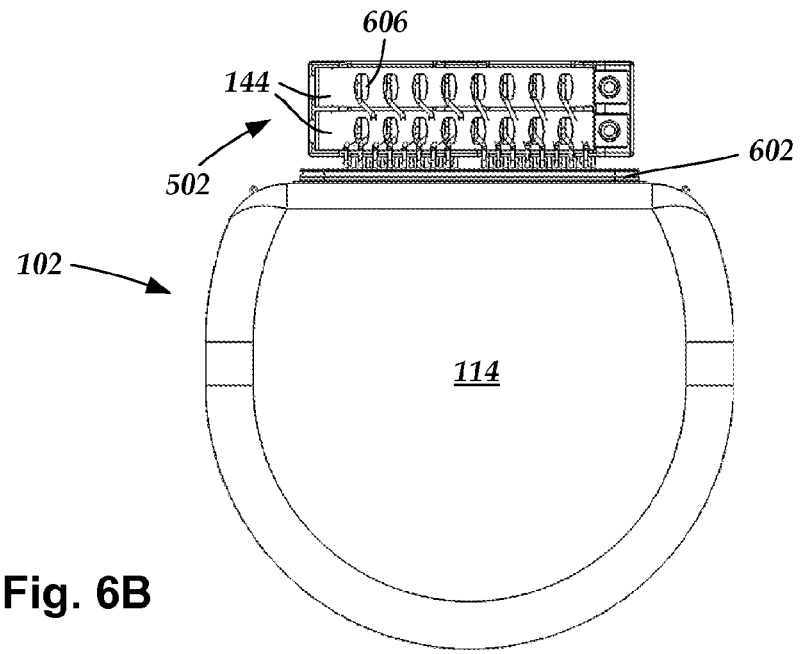
FIG. 6B is a schematic side view of one embodiment of connector assemblies disposed in the connector assembly retainer of FIG. 5A which, in turn, is disposed on the control module of FIG. 1, according to the invention.
Figure 6C:
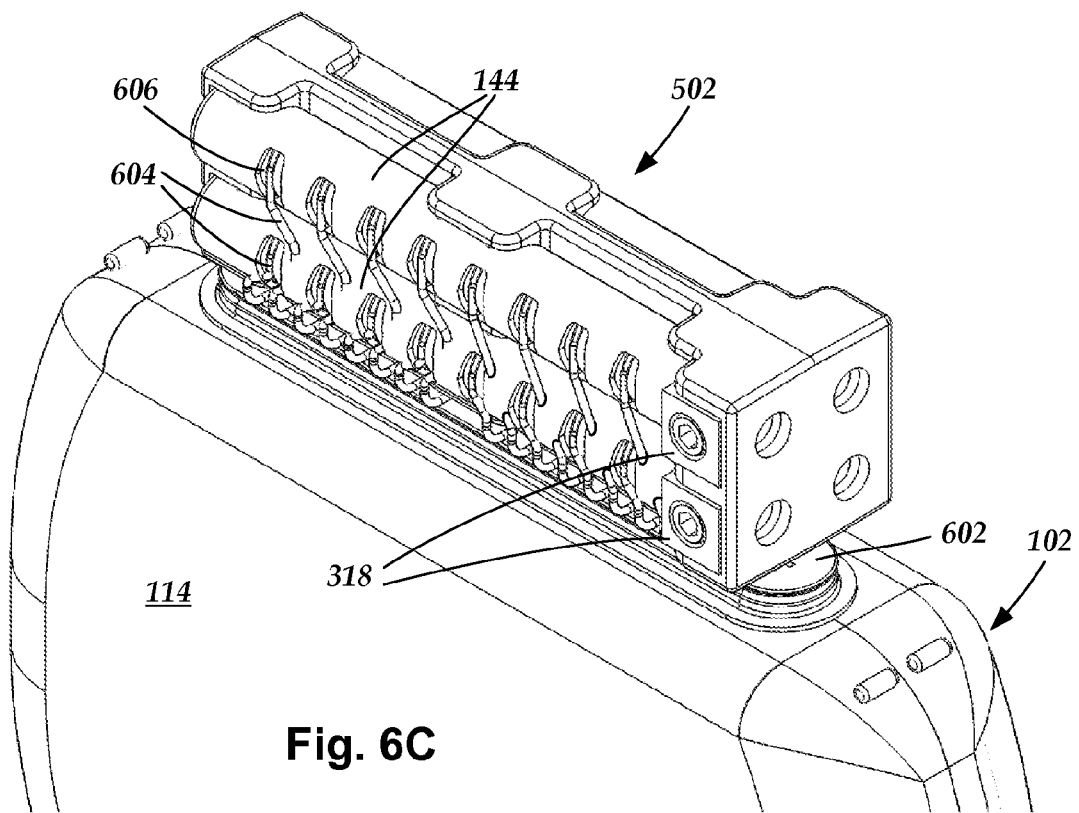
FIG. 6C is a schematic close-up perspective view of one embodiment of connector assemblies disposed in the connector assembly retainer of FIG. 5A which, in turn, is disposed on the control module of FIG. 1, according to the invention.

Turning now to FIGS. 6A-6C, the connector assembly retainer 502 can be coupled to the control module 102. In at least some embodiments, the connector assembly retainer 502 is coupled to an outer surface of the housing 114 of the control module 102. In at least some embodiments, the connector assembly retainer 502 is affixed to the outer surface of the housing 114.

FIG. 6A is a schematic perspective view of one embodiment of connector assemblies 144 disposed in the connector assembly retainer 502 which, in turn, is disposed on the control module 102. FIG. 6B is a schematic side view of one embodiment of connector assemblies 144 disposed in the connector assembly retainer 502. FIG. 6C is a schematic close-up perspective view of one embodiment of connector assemblies 144 disposed in the connector assembly retainer 502. FIGS. 6A-6C omit the header 150, for clarity of illustration.

Connector contacts (316 of FIGS. 3A-3B) disposed within the connector assemblies 144 are electrically coupled to the electronic subassembly (110 of FIGS. 1 and 2) of the control module 102. The connector contacts can be electrically coupled to the electronic subassembly 110 in any suitable manner. In at least some embodiments, the control module 102 includes an electronic interface 602 disposed on the outer surface of the housing 114. The electronic interface 602 provides an electrical connection (e.g., via feedthrough pins, or the like) to the electronic subassembly 110 disposed in the control module 102. One or more control module conductors (e.g., feedthrough interconnects, or the like), such as control module conductors 604, electrically couple the connector contacts 316 disposed within the connector assemblies 144 to the electronic interface 602.

In at least some embodiments, the connector assemblies 144 define one or more connection apertures, such as connection aperture 606, through the connector housing 314 for facilitating connection between the connector contacts 316 and the control module conductors 604. In FIGS. 6A-6C, the connector assembly retainer 502 is shown coupled to the control module 102 in proximity to an electronic interface 602 to facilitate coupling of the connector contacts of the connector assemblies 144 to the electronic interface 602.

Figure 7A:
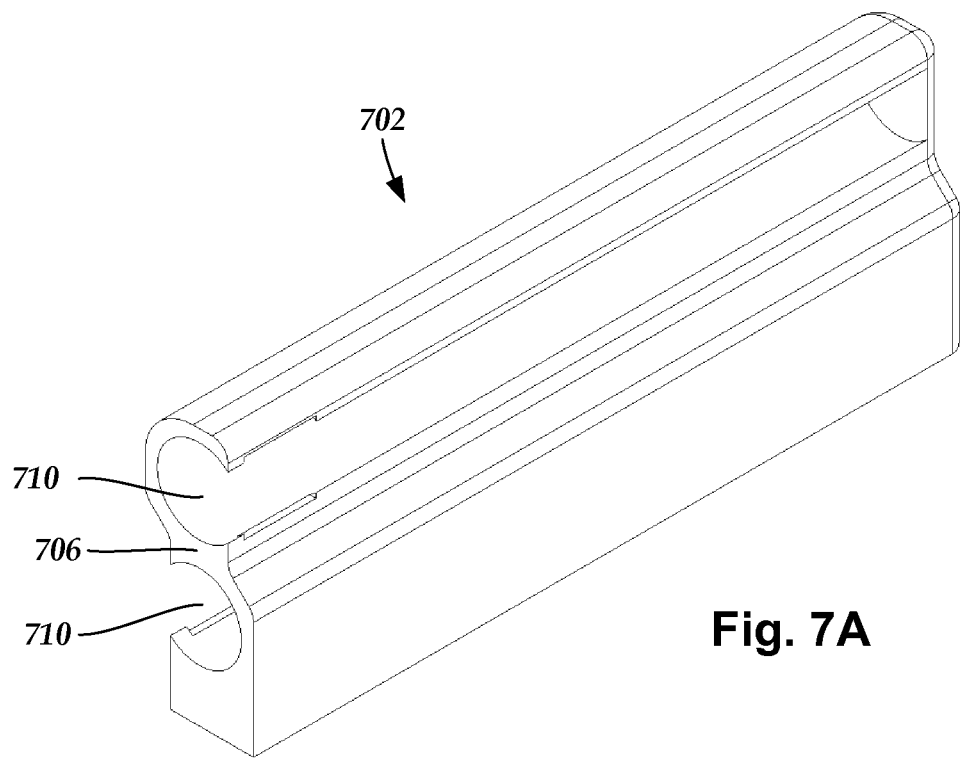
FIG. 7A is a schematic perspective view of another embodiment of a connector assembly retainer suitable for use with the control module of FIG. 1, according to the invention.
Figure 7B:
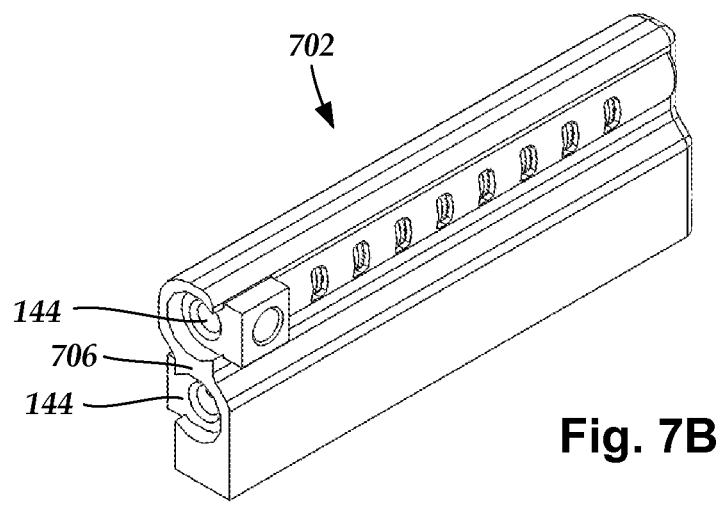
FIG. 7B is a schematic perspective view of one embodiment of connector assemblies disposed in the connector assembly retainer of FIG. 7A, according to the invention.

Turning now to FIGS. 7A-8B, as discussed above the connector assembly retainer 502 can be formed to receive any suitable number of connector assemblies 144. FIG. 7A is a schematic perspective view of another embodiment of a connector assembly retainer 702 configured and arranged to receive up to two connector assemblies 144. FIG. 7B is a schematic perspective view of one embodiment of connector assemblies 144 disposed in the connector assembly retainer 702. The connector assembly retainer 702 defines channels 710 separated from one another by a partition 706. In FIGS. 7A-7B, the channels 710 are defined such that the channels 710 extend along opposing sides of the connector assembly connector 702. In at least some embodiments, the channels 710 are defined such that the channels 710 extend along the same side of the connector assembly connector 702. The connector assembly connector 702 can be formed such that, when the connector assembly retainer 702 is coupled to the control module 102, either one or both of the channels 710 abut the control module 102.

Figure 8A:
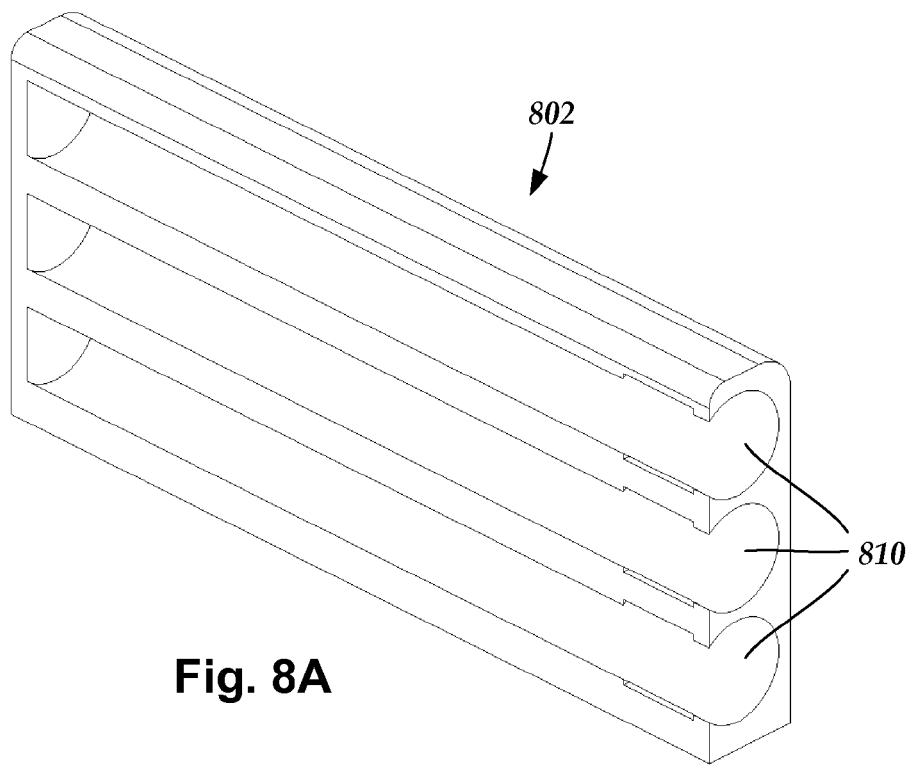
FIG. 8A is a schematic perspective view of yet another embodiment of a connector assembly retainer suitable for use with the control module of FIG. 1, according to the invention.
Figure 8B:
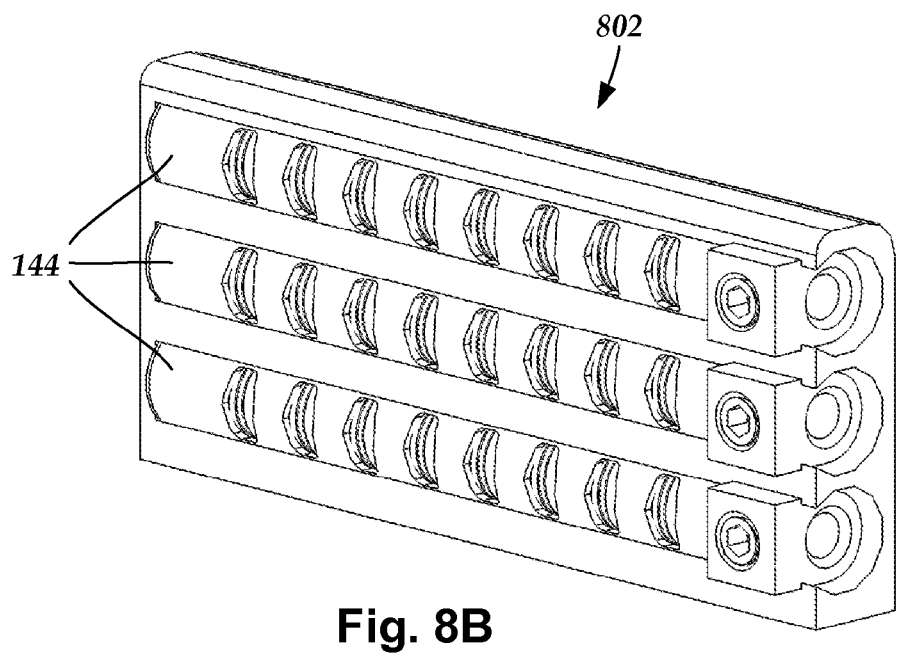
FIG. 8B is a schematic perspective view of one embodiment of connector assemblies disposed in the connector assembly retainer of FIG. 8A, according to the invention.

FIG. 8A is a schematic perspective view of yet another embodiment of a connector assembly retainer 802 configured and arranged to receive up to three connector assemblies 144. FIG. 8B is a schematic perspective view of one embodiment of connector assemblies 144 disposed in the connector assembly retainer 802. The connector assembly retainer 802 defines channels 810. In FIGS. 8A-8B, the channels 710 are defined such that each of the channels extends along the same side of the connector assembly connector 802. In at least some embodiments, the channels 810 are defined such that one or two of the channels 810 extend along a first side of the connector assembly connector 802 and the remaining channels 810 extend along a second side of the connector assembly connector 802 opposite to the first side. The connector assembly connector 802 can be formed such that, when the connector assembly retainer 802 is coupled to the control module 102, any number of the channels 810, up to the total number of the channels 802, abuts the control module 102. In FIGS. 8A-8B, the channels 810 are arranged in a one-by-three arrangement. It will be understood that the channels 810 can be housed in any suitable configuration, such as a one-by-two arrangement.

It will be understood that the connector assembly retainers 702 and 802 can include all, or a portion, of the same features (e.g., end stops, apertures, retention features, channel pockets, and the like or combinations thereof) discussed above, with reference to connector assembly retainer 502. It will also be understood that the connector assembly retainers 702 and 802 can include similar arrangements of the above-mentioned features. It will further be understood that the connector assembly retainers 702 and 802 can include similar connections between connector assemblies 144 and the connector assembly retainers 702 and 802, as well as between the connector assembly retainers 702 and 802 and the control module 102.

Figure 9:
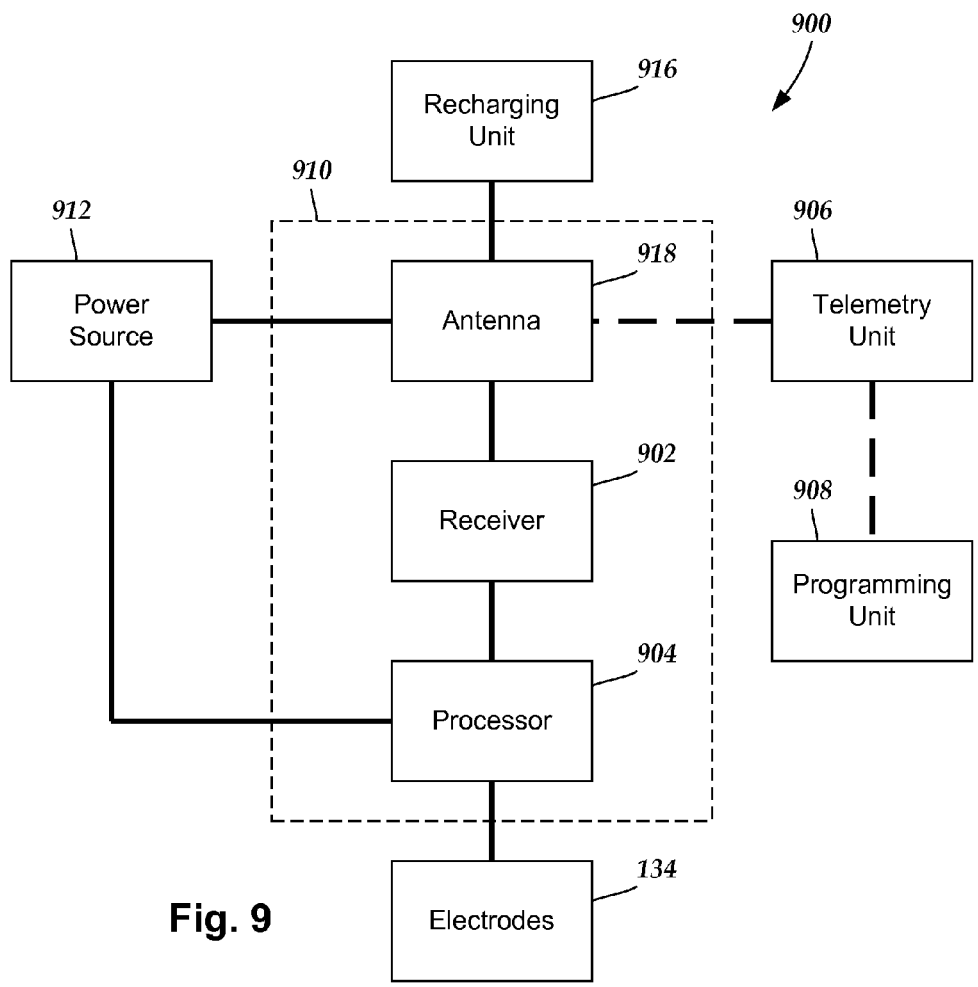
FIG. 9 is a schematic overview of one embodiment of components of a stimulation system, including an electronic subassembly disposed within a control module, according to the invention.

FIG. 9 is a schematic overview of one embodiment of components of an electrical stimulation system 900 including an electronic subassembly 910 disposed within a control module. It will be understood that the electrical stimulation system can include more, fewer, or different components and can have a variety of different configurations including those configurations disclosed in the stimulator references cited herein.

Some of the components (for example, power source 912, antenna 918, receiver 902, and processor 904) of the electrical stimulation system can be positioned on one or more circuit boards or similar carriers within a sealed housing of an implantable pulse generator, if desired. Any power source 912 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 918 or a secondary antenna. The external power source can be in a device that is mounted on the skin of the user or in a unit that is provided near the user on a permanent or periodic basis.

If the power source 912 is a rechargeable battery, the battery may be recharged using the optional antenna 918, if desired. Power can be provided to the battery for recharging by inductively coupling the battery through the antenna to a recharging unit 916 external to the user. Examples of such arrangements can be found in the references identified above.

In one embodiment, current is emitted by the electrodes 134 on the paddle or lead body to stimulate nerve fibers, muscle fibers, or other body tissues near the electrical stimulation system. A processor 904 is generally included to control the timing and electrical characteristics of the electrical stimulation system. For example, the processor 904 can, if desired, control one or more of the timing, frequency, strength, duration, and waveform of the pulses. In addition, the processor 904 can select which electrodes can be used to provide stimulation, if desired. In some embodiments, the processor 904 may select which electrode(s) are cathodes and which electrode(s) are anodes. In some embodiments, the processor 904 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 908 that, for example, allows modification of pulse characteristics. In the illustrated embodiment, the processor 904 is coupled to a receiver 902 which, in turn, is coupled to the optional antenna 918. This allows the processor 904 to receive instructions from an external source to, for example, direct the pulse characteristics and the selection of electrodes, if desired.

In one embodiment, the antenna 918 is capable of receiving signals (e.g., RF signals) from an external telemetry unit 906 which is programmed by a programming unit 908. The programming unit 908 can be external to, or part of, the telemetry unit 906. The telemetry unit 906 can be a device that is worn on the skin of the user or can be carried by the user and can have a form similar to a pager, cellular phone, or remote control, if desired. As another alternative, the telemetry unit 906 may not be worn or carried by the user but may only be available at a home station or at a clinician's office. The programming unit 908 can be any unit that can provide information to the telemetry unit 906 for transmission to the electrical stimulation system 900. The programming unit 908 can be part of the telemetry unit 906 or can provide signals or information to the telemetry unit 906 via a wireless or wired connection. One example of a suitable programming unit is a computer operated by the user or clinician to send signals to the telemetry unit 906.

The signals sent to the processor 904 via the antenna 918 and receiver 902 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 900 to cease operation, to start operation, to start charging the battery, or to stop charging the battery. In other embodiments, the stimulation system does not include an antenna 918 or receiver 902 and the processor 904 operates as programmed.

Optionally, the electrical stimulation system 900 may include a transmitter (not shown) coupled to the processor 904 and the antenna 918 for transmitting signals back to the telemetry unit 906 or another unit capable of receiving the signals. For example, the electrical stimulation system 900 may transmit signals indicating whether the electrical stimulation system 900 is operating properly or not or indicating when the battery needs to be charged or the level of charge remaining in the battery. The processor 904 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A control module for providing electrical stimulation of patient tissue, the control module comprising:
    a control module housing having an outer surface;
    an electronic subassembly disposed in the control module housing;
    an electrical interface disposed along the outer surface of the control module housing, the electrical interface coupled to the electronic subassembly;
    a header disposed along the outer surface of the control module housing over the electrical interface, wherein the header defines a plurality of ports;
    a connector assembly retainer disposed in the header and coupled to the electrical interface, the connector assembly retainer having a first end, a second end, and a longitudinal axis, the connector assembly retainer comprising
        a plurality of channels each extending along the longitudinal axis of the connector assembly retainer, and
        a plurality of apertures defined at the second end of the connector assembly retainer such that each of the plurality of apertures is aligned axially with a different one of the plurality of channels,
    wherein each of the plurality of ports defined in the header is aligned with a different one of the plurality of apertures defined at the second end of the connector assembly retainer; and
    a plurality of connector assemblies each configured and arranged for receiving a lead or lead extension, each of the plurality of connector assemblies releasably disposed in a different one of the plurality of channels of the connector assembly retainer, each of the plurality of connector assemblies comprising
        a connector housing defining a port at one end of the connector assembly, the port configured and arranged for receiving a portion of the lead or lead extension,
        a plurality of spaced-apart connector contacts permanently disposed in the port defined by the connector housing, the plurality of connector contacts each coupled to the electronic subassembly, wherein the plurality of connector contacts are configured and arranged to couple to terminals disposed on the lead or lead extension, and
        at least one solid, electrically-nonconductive spacer disposed between adjacent connector contacts of the plurality of connector contacts.

2. The control module of claim 1, wherein the connector assembly retainer is affixed to the outer surface of the control module housing.

3. The control module of claim 1, wherein the connector assembly retainer further comprises an end stop disposed at a first end of at least one of the plurality of channels.

4. The control module of claim 1 wherein the connector assembly retainer further comprises a plurality of retention features, each of the plurality of retention features configured and arranged to retain one of the plurality of connector assemblies in one of the plurality of channels.

5. The control module of claim 4, wherein at least one of the plurality of retention features comprises at least one of a projection or an enhanced wall feature disposed along at least one of the plurality of channels.

6. The control module of claim 1, wherein the connector assembly retainer further comprises a partition separating at least one of the plurality of channels from at least one other channel of the plurality of channels.

7. The control module of claim 1, wherein at least one of the plurality of connector assemblies comprises a retaining element for retaining leads or lead extensions within the at least one of the plurality of connector assemblies.

8. The control module of claim 7, wherein at least one of the plurality of channels defines a pocket configured and arranged to receive the retaining element disposed on at least one of the plurality of connector assemblies.

9. The control module of claim 1, wherein at least one of the plurality of connector assemblies is releasahly disposed on the connector assembly retainer via a snap connection.

10. The control module of claim 1, wherein at least one of the plurality of connector assemblies is reieasabiy disposed on the connector assembly retainer via an interference fit.

11. The control module of claim 1, wherein the connector assembly retainer comprises two channels.

12. The control module of claim 1, wherein the connector assembly retainer comprises three channels.

13. The control module of claim 1, wherein the connector assembly retainer comprises four channels.

14. The control module of claim 1, wherein the control module further comprises a plurality of control module conductors, each of the plurality of control module conductors electrically coupling the electronic subassembly to a different one of the plurality of spaced-apart connector contacts disposed in the plurality of connector assemblies.

15. The control module of claim 1, wherein the at least one solid, electrically-nonconductive spacer is disposed entirely in the connector housing port between adjacent connector contacts of the plurality of connector contacts.

16. An electrical stimulation system for providing electrical stimulation of patient tissue, the electrical stimulation system comprising:
    the control module of claim 1; and
    at least one lead body, each of the at least one lead body configured and arranged for insertion into a different one of the plurality of connector assemblies of the control module, each of the at least one lead body having a distal end and a proximal curl, the at least one lead body comprising
        a plurality of electrodes disposed at the distal end of the at least one lead body,
        a plurality of terminals disposed at the proximal end of the at least one lead body, and
        a plurality of conductive wires electrically coupling each of the electrodes to at least one of the plurality of terminals.

17. The electrical stimulation system of 16, wherein the number of connector assemblies is equal to the number of lead bodies.

18. The electrical stimulation system of claim 16, wherein the connector assembly retainer comprises at least two channels.

19. The electrical stimulation system of claim 16, wherein the connector assembly retainer further comprises at least one retention feature configured and arranged to retain at least one of the plurality of connector assemblies in at least one of the plurality of channels.

20. An electrical stimulation system for providing electrical stimulation of patient tissue, the electrical stimulation system comprising:
    the control module of claim 1:
    at least one lead extension, each of the at least one lead extension configured and arranged for insertion into a different one of the plurality of connector assemblies of the control module, the at least one lead extension having a distal end and a proximal end, the at least one lead extension comprising a lead extension connector assembly disposed at the distal end of the at least one lead extension and a plurality of lead extension terminals disposed at the proximal end of the at least one lead extension, wherein the lead extension connector assembly comprises a plurality of lead extension connector contacts electrically coupled to the plurality of lead extension terminals; and
    at least one lead body, the at least one lead body configured and arranged for insertion into the lead extension connector assembly, each of the at least one lead body having a distal end and a proximal end, the at least one lead body comprising
        a plurality of electrodes disposed at the distal end of the at least one lead body,
        a plurality of terminals disposed at the proximal end of the at least one lead body, and
        a plurality of conductive wires electrically coupling each of the electrodes to at least one of the plurality of terminals.

* * * * *